United States Patent [19]

Johnson

[11] Patent Number: 4,943,397
[45] Date of Patent: Jul. 24, 1990

[54] METATHESIS OF FUNCTIONAL OLEFINS

[75] Inventor: Thomas H. Johnson, Houston, Tex.

[73] Assignee: Shell Oil Company, Houston, Tex.

[21] Appl. No.: 247,478

[22] Filed: Sep. 22, 1988

[51] Int. Cl.⁵ ............................ C09F 5/00; C09F 7/08
[52] U.S. Cl. ............................ 260/405.5; 260/405.6;
260/410.9 R; 260/413; 560/190; 560/203;
560/262; 560/302; 558/265; 568/564; 568/673;
568/857
[58] Field of Search ............... 560/190, 203, 262, 302;
260/405.5, 405.6, 410.9 R, 546, 413; 558/265;
568/673, 857, 564

[56] References Cited

U.S. PATENT DOCUMENTS

| | | | |
|---|---|---|---|
| 2,501,851 | 3/1950 | Radlove | 260/405.6 |
| 3,065,248 | 11/1962 | Brown et al. | 260/405.6 |
| 3,079,413 | 2/1963 | Moulton et al. | 260/405.6 |
| 3,865,868 | 2/1975 | Lewis | 260/475 N |
| 4,269,780 | 5/1981 | Banasiak | 260/405 |
| 4,371,469 | 2/1983 | Foglia et al. | 260/405.6 |
| 4,480,049 | 10/1984 | Johnson | 502/231 |
| 4,481,145 | 11/1984 | Timms | 260/405.6 |
| 4,489,171 | 12/1984 | Johnson | 502/231 |
| 4,529,815 | 7/1985 | Schneider et al. | 560/205 |
| 4,550,216 | 10/1985 | Basset et al. | 585/645 |
| 4,560,792 | 12/1985 | Banasiak | 560/261 |
| 4,654,462 | 3/1987 | Basset et al. | 585/646 |
| 4,681,956 | 7/1987 | Shrock | 556/12 |
| 4,727,215 | 2/1988 | Shrock | 585/645 |

OTHER PUBLICATIONS

J. of the Amer. Oil Chemist's Society, vol. 51, 1974, pp. 381–384.
Tetrahedron Letters, No. 5, 1977, pp. 441–442.
J. of the Amer. Oil Chemist's Society, vol. 56, 1979, pp. 823A–826A.
J. of Organometallic Chemistry, 255, 1983, pp. 159–171.
J. of the Amer. Oil Chemist's Society, vol. 65, 1985, pp. 888–891.

Primary Examiner—Paul J. Killos

[57] ABSTRACT

The present invention relates to a process for metathesizing an olefin having at least one terminal functional group which comprises contacting said olefin at metathesis conditions with a catalyst comprising: (a) a transition metal selected from tungsten, molybdenum and rhenium, (b) an organometallic compound based on an element selected from aluminum, tin, lead, magnesium and titanium, and (c) an oxophilic agent having a metal-oxygen bond strength greater than the metal-oxygen bond strength of said transition metal.

10 Claims, 1 Drawing Sheet

RATE OF METATHESIS OF METHYL OLEATE AT 60°C o——o WITH OXOPHILIC AGENT
o– – –o WITHOUT OXOPHILIC AGENT

RATE OF METATHESIS OF METHYL OLEATE AT 60°C

METATHESIS OF FUNCTIONAL OLEFINS

FIELD OF THE INVENTION

This invention relates to a process for the metathesis of an olefin having at least one terminal functional group.

BACKGROUND OF THE INVENTION

The metathesis of olefins consists of the exchange of groups adjacent to the double bond; between two olefin molecules, it gives the possibility of producing compounds which are difficult to synthesize by known methods. Metathesis is carried out utilizing heterogeneous or homogeneous catalysts, the catalytic systems generally employed being based upon the transition metals, W, Mo or Re. The reaction can be written diagrammatically as follows:

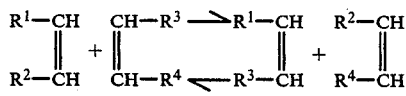

$R^1$ to $R^4$ designate carbon chains or groups, some of which can be the same and which can carry functions, such as for example carboxyls, hydroxyls, amines, nitriles, silyls, halogens, ethers or others.

It is known that tungsten-based and rhenium-based catalyst systems can be utilized for the metathesis of functionalized olefins. The tungsten catalyst system that is known consists of $WCl_6$ activated by a stoichiometric quantity of a tetraalkyltin reagent at 110° C. (J. C. Mol *J. Molec. Catal.* 15 (1982) 35; J. C. Mol *Chem. Tech.* 13 (1983) 250; R. H. A. Bosma, G. C. N. Van den Aardweg and J. C. Mol *J. Organometal. Chem.* 255 (1983) 159). Variations are known such as the catalyst system consisting of $WOCl_4$ activated by $Ti(\eta^5-C_5H_5)_2(CH_3)_2$ (J. Tsuji and S. Hashiguchi *Tet. Lett.* 21 (1980) 2955), $WCl_6$ activated with $BEt_3$ (R. Nakamura, S. Fukuhara, S. Matsumoto and K. Komatsu *Chem. Lett.* (1976) 253; R. Nakamura, S. Matsumoto and E. Echigoya *Chem. Lett.* (1976) 1019), $Mo(OEt)_2Cl_3$ activated by $BEt_3$ (Nakamura) and $WCl_6$ activated by $Al_2Me_3Cl_3$ (Nakamura).

A second catalyst system is a heterogeneous catalyst prepared by depositing $Re_2O_7$ on silica or alumina and activating it with tetraalkyltin reagents (see articles by Mol above). It is active at room temperature.

Despite the previous studies, industrial applications of the metathesis of olefins still suffer from certain deficiencies and require improvements. In particular, the reaction is generally too slow. The invention described herein is, therefore, directed to a process for the metathesis of functionalized olefins utilizing an improved catalyst system which results in an increased rate of metathesis.

SUMMARY OF THE INVENTION

The present invention relates to a process for metathesizing an olefin having at least one terminal functional group which comprises contacting said olefin at metathesis conditions with a catalyst comprising: (a) a transition metal selected from tungsten, molybdenum and rhenium, (b) an organometallic compound based on an element selected from aluminum, tin, lead, magnesium and titanium, and (c) an oxophilic agent having a metal-oxygen bond strength greater than the metal-oxygen bond strength of said transition metal.

DESCRIPTION OF THE PREFERRED EMBODIMENTS

Figure 1:
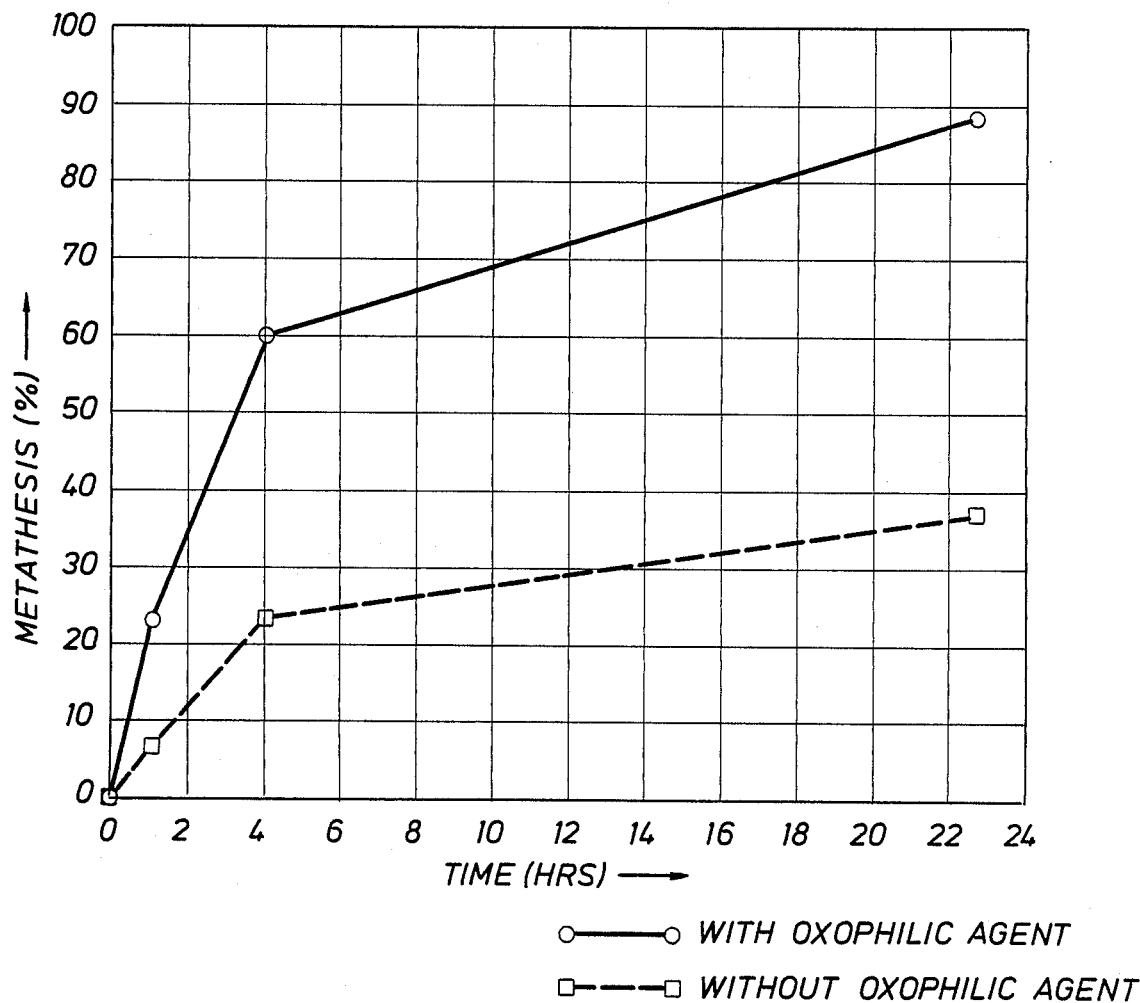
FIG. 1 is a graphic comparison of the rates of metathesis of methyl oleate for a catalyst system prepared according to the invention and a catalyst system not prepared according to the invention.

The present invention provides a process for the metathesis of olefins having at least one terminal functional group which comprises contacting said olefin at metathesis conditions with a catalyst comprising a metathesis transition metal selected from tungsten, molybdenum and rhenium, an organometallic compound based on an element selected from aluminum, tin, lead, magnesium and titanium, and an oxophilic agent having a metal-oxygen bond strength greater than the metal-oxygen bond strength of the metathesis transition metal utilized in the catalyst system.

The present invention deals with the metathesis of an olefin having at least one terminal functional group selected from groups having the formulas

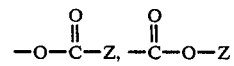

and O-Z wherein Z is a hydrocarbyl group having 1 to about 20 carbon atoms, a hydrocarbyloxy group having 1 to about 20 carbon atoms or hydrogen. Preferably, Z is a hydrocarbyl group although Z can be any substituent which does not interfere with the reaction. Thus, suitable functional olefins include alkylene acid esters, alkylene esters, alkylene ethers, alkylene anhydrides, alkylene carbonates, dialkylene alkyl glycerides, alkylene dialkyl glycerides and trialkylene glycerides. The preferred functional olefins are those wherein the olefinic hydrocarbyl portion thereof has the formula $Z'$—$CH$=$CH(CH_2)_n$— wherein n is in the range of 2 to 20 and $Z'$ is hydrogen or alkyl radical having 1 to 20 carbon atoms. It is also within scope of the present invention to use a functional olefin having two terminal functional groups of the types described above. It is further within the scope of the present invention to use a monoolefin or a polyolefin having at least one terminal functional group. Typically, the preferred functional olefins contain no more than about 30 carbon atoms per molecule. Suitable functional olefins for use in the process of the instant invention include methyl oleate, oleyl acetate, methyl non-8-enoate, ethyl dec-9-enoate and the like.

The metathesis of functionalized olefins is well known to be more difficult than the metathesis of non-functionalized olefins. Many olefin metathesis catalysts are not active with functionalized olefin substrates and those that are active often give low conversions and/or low rates of reaction. The three most widely used metals in olefin metathesis are tungsten, molybdenum and rhenium. Each of these three metals has an affinity for oxygen. While not intending to be bound by any particular theory, it is hypothesized that one mode of catalyst deactivation in the metathesis of functionalized olefins, especially oxygen-containing olefins, is the interaction of the metathesis metal, i.e., tungsten, molybdenum and/or rhenium, with the substrate oxygen. If all of the metals are tied up with the substrate oxygen, none of the metal would be available to complex with the olefin site of the substrate and no metathesis would take place. If an equilibrium existed between the oxygen and the olefin metal complexes, then the rate of reaction would be reduced. Therefore, adding to the catalyst system a metal more oxophilic that the metathesis metal should force the metathesis metal to preferentially complex with the olefin site of the substrate and result in more and/or faster metathesis of a functionalized olefin.

The catalyst system utilized in the present invention comprises a metathesis transition metal selected from the group consisting of tungsten, molybdenum, rhenium and mixtures thereof, an organometallic compound based on a metal selected from the group consisting of aluminum, tin, lead, magnesium, titanium and mixtures thereof, and an oxophilic agent having a metal-oxygen bond strength greater than the metal-oxygen bond strength of said metathesis transition metal. The metathesis transition metal component is typically an oxide, chloride or bromide of tungsten, molybdenum or rhenium such as, for example, tungsten hexachloride. The organometallic compound is typically an alkyl group combined with aluminum, tin, lead, magnesium, or titanium such as, for example, $R_4Sn$ wherein R is alkyl, i.e., $CH_3$, $C_2H_5$ and $C_4H_9$.

The oxophilic agent can be any metal-containing compound wherein said metal has a metal-oxygen bond strength greater than the metal-oxygen bond strength of the metathesis transition metal used in the catalyst. The oxophilic agent component of the catalyst has the general formula M—X wherein M is zironium, samarium, lanthanum and the like, or any other metal having a metal-oxygen bond strength greater than the metal-oxygen bond strength of the metathesis transition metal and X comprises one or more organic or inorganic species which in combination neutralize the charge of M and does not interfere with the reaction. It is understood that other ligand or complex-forming neutral components may be present. A list of oxygen-metal bond strengths is presented in Table I.

TABLE I

| Molecule | Strengths of Chemical Bonds[1] Kcal mole$^{-1}$ | Molecule | Kcal mole$^{-1}$ |
|---|---|---|---|
| O—Mg | 83 | O—Cd | 89 |
| O—Al | 107 | O—In | 77 |
| O—Ca | 88 | O—Sn | 125 |
| O—Sc | 162 | O—Sb | 93 |
| O—Ti | 167 | O—Te | 91 |
| O—V | 149 | O—I | 47 |
| O—Cr | 102 | O—Ba | 125.9 |
| O—Mn | 97 | O—La | 192 |
| O—Fe | 99 | O—Ce | 186 |
| O—Co | 87.3 | O—Pr | 172 |
| O—Ni | 87.4 | O—Nd | 167 |
| O—Cu | 96 | O—Gd | 162 |
| O—Zn | 66 | O—Yb | 123 |
| O—Ga | 70 | O—Hf | 176 |
| O—Ge | 157 | O—Ta | 198 |
| O—Sr | 96 | O—W | 155 |
| O—Y | 170 | O—Os | 123 |
| O—Zr | 182 | O—Pb | 99 |
| O—Nb | 162 | O—Th | 197 |
| O—Mo | 117 | O—Bi | 72 |
| O—Ru | 43 | O—U | 180 |
| O—Ag | 47 | O—Np | 172 |

[1]CRC Handbook of Chemistry and Physics, 50th Edition, 1969-1970, F-158 and F159

Examples of suitable species for X include sulfate, phosphate, cyclopentadienyl and the like, with sulfate being preferred for heterogeneous catalysts and cyclopentadienyl being preferred for tungsten-based homogeneous catalysts.

One preferred class of oxophilic agents in the catalyst system in the instant invention are the metallocenes. Metallocenes are organometallic compounds which are cyclopentadienyl derivatives of zirconium, samarium, lanthanum and the like and include mono-, di- and tricyclopentadienyls derivatives of zirconium, samarium, lanthanum and the like. A preferred metallocene has the general formula $(cyclopentadienyl)_n MY_{4-n}$ wherein M is zirconium, samariium, or lanthanum, Y is individually selected from the group consisting of hydrogen, a $C_1$–$C_5$ alkyl group, a $C_6$–$C_{20}$ aryl group, a $C_1$–$C_5$ metalloalkyl group and halogen or a group of the following formula:

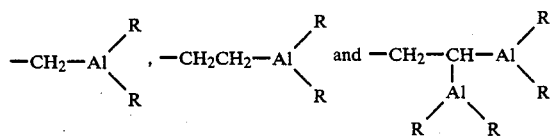

in which R is hydrogen, a $C_1$–$C_5$ alkyl group or a $C_1$–$C_5$ metalloalkyl group, and n is an integer ranging from 1 to 4.

By way of example, zirconium metallocenes are called zirconocenes. Suitable zirconocenes are bis(cyclopentadienyl)zirconium dichloride, bis(cyclopentadienyl)zirconium methyl chloride, bis(cyclopentadienyl zirconium dimethyl, bis(methylcyclopentadienyl)zirconium dichloride, bis(methylcyclopentadienyl)zirconium methyl chloride, bis(methylcyclopentadienyl)zirconium dimethyl, bis(pentamethylcyclopentadienyl)zirconium dichloride, bis(pentamethylcyclopentadienyl)zirconium methyl chloride, bis(pentamethylcyclopentadienyl)zirconium dimethyl, bis(n-butylcyclopentadienyl)zirconium dichloride, bis(n-butylcyclopentadienyl)zirconium methyl chloride, bis(n-butylcyclopentadienyl)zirconium dimethyl.

The molar ratios of the components in the catalyst system can vary over a wide range with varying effects upon yield and selectivity. Typically, the molar ratio of the organometallic component to the metathesis transition metal component is in the range of from about 0.1:1.0 to about 10.0:1.0, preferably from about 1.0:1.0, and the molar ratio of the oxophilic agent to the metathesis transition metal component is in the range of from about 0.1:1.0 to about 1000:1.0, preferably from about 1.0:1.0.

The amount of catalyst employed in the process of this invention can be expressed in terms of the molar ratio of olefin to catalyst. Generally, the molar ratio of the olefin reactant to the catalyst system is in the range of from about 1.0:1.0 to about 1,000,000:1.0, preferably from about 1.0:1.0 to about 100,000:1.0, and more preferably from about 100:1.0 to about 10,000:1.0.

The metathesis of the functionalized olefins can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is generally carried out at temperatures ranging from about 0° C. to about 350° C., preferably from about 0° C. to about 200° C., and at pressures in the range of from 14 psig to about 1000 psig, preferably from about 14 psig to about 500 psig. The metathesis reaction is usually effected in a liquid phase and if desired, liquid reaction diluents are utilized. Examples of suitable diluents are hydrocarbons free from aliphatic unsaturation, such as acyclic or alicyclic alkanes of from about 6 to about 12 carbon atoms, i.e. hexane, isooctane and cyclohexane. Also exemplary would be monoaromatic compounds such as benzene, chlorobenzene and toluene. If the diluent is added, it is present in an amount of about 100 moles of diluent per mole of olefinic reactants, preferably about 20 moles of diluent per mole of olefinic reactant.

The presence of molecular oxygen and water has been found to be deleterious to the metathesis reaction and should be substantially avoided during the reaction. Inert gases such as nitrogen, argon or helium can be used to maintain a dry, inert atmosphere during the reaction.

In the metathesis reaction, a purification step to remove impurities such as, for example, hydroperoxides and residual alcohols or acids, by such methods as filtering through silica gel or alumina and storing over molecular sieves or distilling from suitable drying agents is beneficial.

The operable range of contact time for the process of this invention depends primarily upon the operating temperature and the activity of the catalyst, promoter concentration, activation temperature, etc. Suitable combinations of contact time and temperature can be selected to alter the distribution of products as desired. With proper selection of conditions and contact times, very high efficiency of conversion of desired products can be obtained.

With a fixed bed reactor, continuous flow operation typically is conducted at pressures in the range of from about 1.0 psig to about 2000 psig, preferably from about 50 psig to about 500 psig, and at temperatures in the range of from about 0° C. to about 500° C., preferably about 100° C. to about 250° C., with weight hourly space velocities in the range of from about 0.1 to about 20.0 parts by weight of olefinic feed per part by weight of catalyst per hour. The space velocity is adjusted according to the presence of inert diluents, changes in density of feed due to change of pressure or temperature, and variation in reaction temperature and the activity of the catalyst. The higher space velocities in general are associated with higher reaction temperatures.

The metathesis of functionalized olefins according to the present invention results in the production of linear alpha, omega difunctional molecules comprising a mixture of difunctional molecules and internal olefins. The difunctional molecules prepared according to the invention are useful as adhesives and crosslinking agents in the conversion of polymers to elastomeric materials.

In a preferred embodiment, methyl oleate is contacted at metathesis conditions, i.e., a temperature in the range between about 0° C. and about 200° C. and a pressure in the range between about 14 psig and about 1000 psig, with a catalyst comprising a transition metal selected from tungsten, molybdenum and rhenium an organometallic compound based on a metal selected from aluminum, tin, lead, magnesium and titanium, and an oxophilic agent having a metal-oxygen bond strength greater than the metal-oxygen bond strength of the transition metal utilized to form a mixture of alkene dioates and alkenes.

The process of the instant invention will be further described below by the following examples which are illustrative and which are not be construed as limiting the scope of the invention.

EXAMPLE 1

The metathesis reaction was loaded and run in a Vacuum Atmospheres dry box. The chlorobenzene (Aldrich, HPLC) and olefins were purged with nitrogen for several hours and stored in the dry box. The methyl oleate (Aldrich, Tech) was vacuum distilled using a 3" ID Oldershaw column with 20 plates and operated at a 2:1 reflux ratio. Material boiling between 662°–683° F. (ca 60%) was used as "methyl oleate" feed. Analysis by GC/MS showed the feed to typically be 95-97% methyl oleate containing the following impurities: methyl stearate, methyl palmitoleate, methyl palmate, and methyl myristate. GC analysis of the metathesis reactions were performed using a 60 meter "x" 0.2 mm ID fused silica capillary column operated at 150° C. for 4 minutes and then temperature programmed at a rate of 15° C./minute to 300° C. was obtained and held there for 30 minutes. A split ratio of 10:1 was employed.

To a 250 ml Erlenmeyer flask equipped with a magnetic stirrer, Claisen adapter, thermometer, and loose stopper (CAUTION: the stopper is loosely position to allow for a release of pressure should any build up) were added 150 ml of chlorobenzene, 0.52 g (1.25 mmol) of $WCl_6$ and 0.2 ml (1.5 mmol) of $Me_4Sn$. This solution was stirred for 30 minutes at 60° C., and then 3.6 g (12.5 mmol) of bis(cyclopentadienyl) zirconium was added. After stirring was continued for another 10 minutes, 3.25 g (12.5 mmol) of isomerized octadecenoates was added. The reaction was stirred at 60° C. Samples were taken for analysis at 1, 4, and 19 hours. Analysis for the disappearance of methyl oleate or octadecene was performed by GC as described above. The results are presented in FIG. I.

EXAMPLE 2

The procedure of Example 1 was followed with the exception that the catalyst system contained no bis(cyclopentadienyl) zirconium. The results are presented in FIG. 1.

I claim as my invention:

1. A process for metathesizing an olefin having at least one terminal functional group wherein said terminal functional group is selected from groups having the formulas

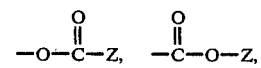

and O—Z wherein Z is selected from a hydrocarbyl group having from 1 to about 20 carbon atoms, a hydrocarbyloxy group having from 1 to about 20 carbon atoms and hydrogen, which comprises contacting said olefin at metathesis conditions with a catalyst comprising: (a) an oxide, chloride or bromide of a transition metal selected from tungsten, molybdenum and rhenium, (b) an organometallic compound based on an element selected from aluminum, tin, lead, magnesium and titanium, in combination with an alkyl group, and (c) an oxophilic agent having a metal-oxygen bond strength greater than the metal-oxygen bond strength of said transition metal and wherein said oxophilic agent is selected from compounds having a formula M—X wherein M is selected from zirconium, samarium, lanthanum and mixtures thereof, and X comprises one or more organic or inorganic species which in combination neutralize M.

2. The process of claim 1 wherein said transition metal component is tungsten hexachloride.

3. The process of claim 2 wherein said organometallic compound is $R_4Sn$ wherein R is an alkyl group.

4. The process of claim 2 or 3 wherein said oxophilic agent is a metallocene.

5. The process of claim 1 wherein said transition metal is rhenium.

6. The process of claim 5 wherein said organometallic compound is $R_4Sn$ wherein R is an alkyl group.

7. The process of claim 5 or 6 wherein said oxophilic agent is $Zr(SO_4)_2$.

8. The process of claim 1 wherein said metathesis conditions include a temperature in the range of from about 0° C. to about 300° C. and a pressure in the range of from about 14 psig to about 1000 psig.

9. The process of claim 1 wherein said olefin contains about 2 to about 30 carbon atoms.

10. The process of claim 9 wherein said olefin is selected from the group consisting of methyl oleate, oleyl acetate, methyl non-8-enoate and ethyl 9 dec-9-enoate.

* * * * *